United States Patent
Tooke, III et al.

(10) Patent No.: US 7,617,114 B1
(45) Date of Patent: Nov. 10, 2009

(54) HEALTH CARE REIMBURSEMENT

(75) Inventors: Charlton Clinton Tooke, III, Ft Lauderdale, FL (US); Charles W. Pomeroy, Alexanderia, VA (US); Douglas M. Kronenberg, Prospect, KY (US)

(73) Assignee: Wellpoint Inc., Indianapolis, IN (US)

( * ) Notice: Subject to any disclaimer, the term of this patent is extended or adjusted under 35 U.S.C. 154(b) by 1477 days.

(21) Appl. No.: 10/354,150

(22) Filed: Jan. 30, 2003

Related U.S. Application Data

(63) Continuation-in-part of application No. 09/924,952, filed on Aug. 9, 2001, now abandoned.

(60) Provisional application No. 60/352,553, filed on Jan. 31, 2002, provisional application No. 60/224,279, filed on Aug. 10, 2000.

(51) Int. Cl.
G06Q 50/00 (2006.01)
G06Q 40/00 (2006.01)

(52) U.S. Cl. ............................................. 705/2; 705/4

(58) Field of Classification Search ...................... 705/2
See application file for complete search history.

(56) References Cited

U.S. PATENT DOCUMENTS

| | | | |
|---|---|---|---|
| 4,491,725 A * | 1/1985 | Pritchard .......................... 705/2 |
| 4,858,121 A | 8/1989 | Barber et al. |
| 5,239,460 A | 8/1993 | LaRoche |
| 5,301,105 A | 4/1994 | Cummings, Jr. |
| 5,359,509 A | 10/1994 | Little et al. |
| 5,361,202 A | 11/1994 | Doue |
| 5,500,795 A | 3/1996 | Powers et al. |
| 5,532,464 A * | 7/1996 | Josephson et al. ............ 235/379 |
| 5,550,734 A * | 8/1996 | Tarter et al. ...................... 705/2 |
| 5,713,485 A * | 2/1998 | Liff et al. .......................... 221/2 |
| 5,758,095 A * | 5/1998 | Albaum et al. ................... 705/2 |
| 5,772,585 A | 6/1998 | Lavin et al. |
| 5,832,447 A | 11/1998 | Rieker et al. |
| 5,924,074 A | 7/1999 | Evans |
| 6,005,942 A | 12/1999 | Chan et al. |
| 6,044,352 A * | 3/2000 | Deavers ........................... 705/4 |
| 6,078,894 A | 6/2000 | Clawson et al. |
| 6,092,096 A | 7/2000 | Lewis |
| 6,108,641 A * | 8/2000 | Kenna et al. .................. 705/35 |
| 6,208,973 B1 | 3/2001 | Boyer et al. |
| 6,249,809 B1 * | 6/2001 | Bro .............................. 709/217 |

(Continued)

OTHER PUBLICATIONS

Anonymous, Flex administrators face opportunities, challenges, Employee Benefit Plan Review, v 56 , n 2, p. 28, Friday, Aug. 31, 2001.*

(Continued)

*Primary Examiner*—C. Luke Gilligan
*Assistant Examiner*—Tran Nguyen
(74) *Attorney, Agent, or Firm*—Roberts, Mlotkowski, Safran & Cole, PC

(57) ABSTRACT

In general, variations that occur when health care resources are allocated based on dated information may be corrected by receiving a report of a health care transaction to be processed by a health care intermediary administering a health savings account, determining that the health care transaction creates a variation when the health care transaction was initiated based on an indicated status that is different from the actual status of the health savings account, and resolving the variation by interfacing with the health resource provider to correct the variation.

21 Claims, 9 Drawing Sheets

U.S. PATENT DOCUMENTS

| | | | |
|---|---|---|---|
| 6,283,761 | B1 | 9/2001 | Joao |
| 6,341,265 | B1 | 1/2002 | Provost et al. |
| 6,343,271 | B1 | 1/2002 | Peterson et al. |
| 6,375,574 | B1 | 4/2002 | Young et al. |
| 6,401,079 | B1 | 6/2002 | Kahn et al. |
| 6,453,297 | B1 | 9/2002 | Burks et al. |
| 6,459,787 | B2 | 10/2002 | McIllwaine et al. |
| 6,478,736 | B1 | 11/2002 | Mault |
| 6,490,620 | B1 | 12/2002 | Ditmer et al. |
| 6,591,260 | B1 | 7/2003 | Schwarzhoff et al. |
| 6,635,088 | B1 | 10/2003 | Hind et al. |
| 6,675,354 | B1 | 1/2004 | Claussen et al. |
| 6,704,736 | B1 | 3/2004 | Rys et al. |
| 6,735,569 | B1 | 5/2004 | Wizig |
| 6,754,640 | B2 * | 6/2004 | Bozeman .................... 705/40 |
| 6,760,861 | B2 | 7/2004 | Fukuhara et al. |
| 6,775,377 | B2 | 8/2004 | McIllwaine et al. |
| 6,785,685 | B2 | 8/2004 | Soetarman et al. |
| 6,847,711 | B2 | 1/2005 | Knott et al. |
| 6,879,959 | B1 | 4/2005 | Chapman et al. |
| 6,882,723 | B1 | 4/2005 | Peterson et al. |
| 6,889,360 | B1 | 5/2005 | Ho et al. |
| 6,925,631 | B2 | 8/2005 | Golden |
| 7,133,840 | B1 | 11/2006 | Kenna et al. |
| 2001/0027402 | A1 | 10/2001 | Ramsaroop |
| 2001/0032099 | A1 | 10/2001 | Joao |
| 2001/0032120 | A1 | 10/2001 | Stuart et al. |
| 2002/0010597 | A1 | 1/2002 | Mayer et al. |
| 2002/0013717 | A1 | 1/2002 | Ando et al. |
| 2002/0032583 | A1 | 3/2002 | Joao |
| 2002/0065758 | A1 | 5/2002 | Henley |
| 2002/0077869 | A1 | 6/2002 | Doyle et al. |
| 2002/0083371 | A1 | 6/2002 | Ramanathan et al. |
| 2002/0128879 | A1 * | 9/2002 | Spears .................... 705/4 |
| 2002/0144187 | A1 | 10/2002 | Morgan et al. |
| 2002/0147632 | A1 | 10/2002 | Winham et al. |
| 2002/0152097 | A1 | 10/2002 | Javors |
| 2003/0046142 | A1 | 3/2003 | Eitel et al. |
| 2003/0050802 | A1 | 3/2003 | Jay et al. |
| 2003/0163365 | A1 | 8/2003 | Farnes et al. |
| 2003/0200118 | A1 | 10/2003 | Lee et al. |
| 2003/0208391 | A1 | 11/2003 | Dvorak et al. |
| 2003/0225690 | A1 | 12/2003 | Eaton |
| 2004/0153337 | A1 | 8/2004 | Cruze |
| 2005/0060197 | A1 | 3/2005 | Mayaud |
| 2006/0047566 | A1 | 3/2006 | Fleming et al. |
| 2006/0136173 | A1 | 6/2006 | Case et al. |
| 2006/0238610 | A1 | 10/2006 | Teesdale |

OTHER PUBLICATIONS

Office Action dated Feb. 10, 2006 from U.S. Appl. No. 09/924,952, 16 pages.

Office Action dated Aug. 24, 2006 from U.S. Appl. No. 09/924,952, 14 pages.

Office Action dated Jan. 29, 2007 from U.S. Appl. No. 09/924,952, 19 pages.

U.S. Appl. No. 11/968,448, filed Jan. 2, 2008.

* cited by examiner

HEALTH CARE REIMBURSEMENT

CROSS-REFERENCE TO RELATED APPLICATIONS

This application claims priority to U.S. Provisional Application No. 60/352,553, titled "Health Care Reimbursement for Advances to Consumers" and filed Jan. 31, 2002; and is a continuation-in-part of U.S. application Ser. No. 09/924,952, titled "Medical Transaction System" filed Aug. 9, 2001, now abandoned, which claims priority to U.S. Provisional Application No. 60/224,279, titled "Online Healthcare System" and filed Aug. 10, 2000. Each of these applications is incorporated by reference in its entirety herein.

TECHNICAL FIELD

This document relates generally to allocating health care resources and more particularly to allocating health care resources from an online health care account to reimburse a health care provider.

BACKGROUND

The health care industry faces several challenges in the desire to remain financially viable while still providing the highest quality health care to consumers. Health insurance providers are under increased pressure to become more flexible and responsive while still maintaining adequate safeguards in managing limited health care resources. For example, some health maintenance organizations require patients to see a primary care physician before being routed to a specialist as a measure of controlling costs. Health care consumers face rising costs in the form of increased premiums, while managed care programs limit available health care opportunities. Health care providers typically face delays in receiving reimbursement for provided health care, as the claims process can be time consuming.

DESCRIPTION OF DRAWINGS

Like reference symbols in the various drawings indicate like elements.

DETAILED DESCRIPTION

Figure 1:
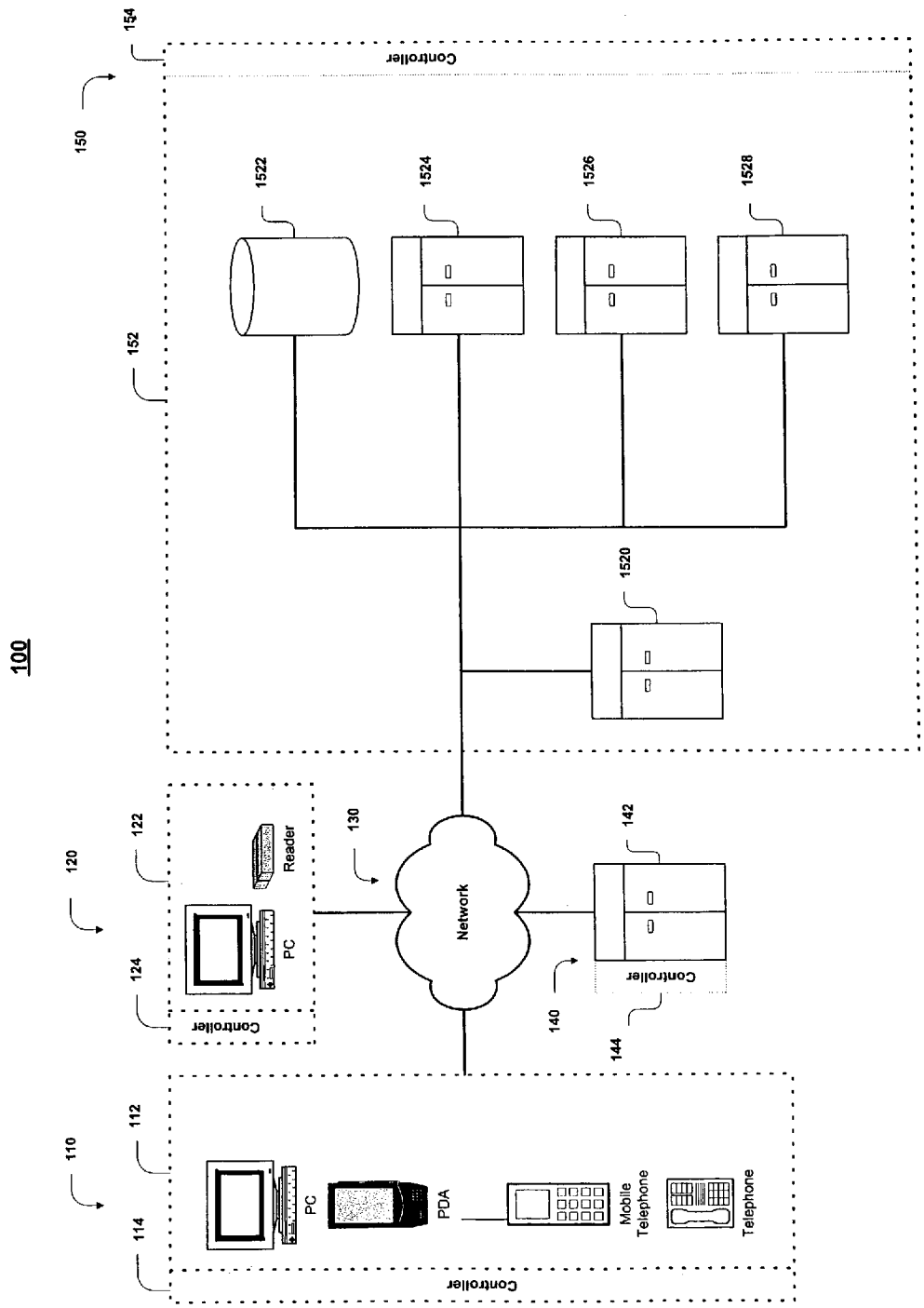
FIG. 1 is a diagram of a health care system structured and arranged to enable a health care consumer to reimburse a health care provider from an online health care account.

FIG. 1 illustrates an exemplary computer system 100 for implementing techniques to reimburse a health care provider in an automated manner. For brevity, several elements in the figure are represented as monolithic entities. However, these elements each may include numerous interconnected computers and components designed to perform a set of specified operations.

As shown, the computer system 100 includes a client system 110 connected to a health care provider ("HCP") system 120 through a network 130. The client system also is connected through the network 130 to a payment host 140 and a health care intermediary 150. The client system 110, the HCP system 120, the payment host 140, and the health care intermediary 150 are configured to request and receive information (e.g., electronic data) from each other through the network 130. The health care intermediary 150 may include and/or form part of an information delivery system, such as, for example, the Internet, the World Wide Web, an online service provider, and/or any other analog or digital wired and/or wireless network that provides information. Such information systems may support a variety of online services including Internet and/or web access, e-mail, instant messaging, paging, chat, interest groups, audio and/or video streaming, and/or directory services.

In general, the client system 110 includes a computer system having hardware and/or software components for communicating with the HCP system 120, the payment host 140, and the health care intermediary 150 through the network 130. The client system 110, the HCP system 120, the payment host 140, and the health care intermediary 150 each may include one or more general-purpose computers (e.g., personal computers and/or servers), one or more special-purpose computers (e.g., devices specifically programmed to communicate with each other), or a combination of one or more general-purpose computers and one or more special-purpose computers. The client system 110, the HCP system 120, the payment host 140, and the health care intermediary 150 may be structured and arranged to communicate using various communication protocols (e.g., HTTP ("Hyper Text Transfer Protocol"), WAP ("Wireless Applications Protocol")) and encapsulation protocols (e.g., UDP ("User Data Protocol")) to establish connections (e.g., peer-to-peer) between network elements and/or to operate within or in concert with one or more other systems (e.g., the Internet and/or Web).

In one implementation, the client system 110, the HCP system 120, the payment host 140, and the health care intermediary 150 each include a device (e.g., client device 112, HCP device 122, payment host device 142, and health care intermediary device 152) operating under the command of a controller (e.g., client controller 114, HCP controller 122, payment host 140, controller 144, and health care intermediary controller 154). An example of a device is a general-purpose computer capable of responding to and executing instructions in a defined manner. Other examples include a special-purpose computer, a personal computer ("PC"), a workstation, a server, a laptop, a Web-enabled telephone, a Web-enabled personal digital assistant ("PDA"), an interactive television set, a set top box, or any other component, machine, tool, equipment, or some combination thereof capable of responding to and executing instructions.

An example of a controller is a software application (e.g., operating system, browser application, micro-browser application, server application, proxy application, gateway application, tunneling application, e-mail application, instant messaging client, online service provider client application, interactive television client application, and/or ISP client) loaded on a device commanding and directing communications enabled by the device. Other examples include a computer program, a piece of code, an instruction, another device, or some combination thereof, for independently or collectively instructing the device to interact and operate as desired. The controller may be embodied permanently or temporarily in any type of machine, component, physical or virtual equipment, storage medium, or propagated signal capable of providing instructions to a device. In particular, the controller (e.g., software application, computer program) may be stored on a storage media or device (e.g., ROM, magnetic diskette, or propagated signal) readable by a general or special purpose programmable computer, such that if the storage media or device is read by a computer system, the functions described herein are performed.

In general, the client system 110 is associated with a health care consumer (e.g., patient, guardian of patient) and is used by the health care consumer to communicate with the HCP system 120, the payment host 140, and/or the health care intermediary 150. For example, the health care consumer can use a client device 112 (e.g., Internet-enabled PDA) for wireless communication with the health care intermediary 150 while at the location of the health care provider.

The HCP system 120 is associated with a health care provider (e.g., doctor, nurse, pharmacist, or other health care professional) that provides health care products (e.g., medication, medical devices) and/or health care services (e.g., surgery, therapy). The health care provider may provide such health care products and services at a fixed location (e.g., hospital, office, nursing home, pharmacy) or at the home of a health care consumer. In general, the HCP system 120 is used by the health care provider to communicate with the client system 110, the payment host 140, and/or the health care intermediary 150. For example, the health care provider can use a HCP device 122 (e.g., PC, credit card reader) for communication with the payment host 140 while a health care consumer is at the location of the health care provider.

The network 130 may include one or more delivery systems for directly or indirectly connecting the client system 110, the HCP system 120, the payment host 140, and the health care intermediary 150 irrespective of physical separation. Examples of delivery systems include, but are not limited to, a local area network ("LAN"), a wide area network ("WAN"), the Internet, the Web, a telephony network (e.g., analog, digital, wired, wireless, PSTN, ISDN, or xDSL), a radio network, a television network, a cable network, a satellite network, and/or any other wired or wireless communications network configured to carry data. Each network may include one or more elements, such as, for example, intermediate nodes, proxy servers, routers, switches, adapters, and wired or wireless data pathways, configured to direct and/or deliver data. Implementations of the network 140 may include various combinations of the different types of networks described above. For example, the HCP system 120 may communicate with the payment host 140 over a telephone network using a credit card processing machine while the client system 110 and the payment host 140 communicate with the health care intermediary 150 over the Internet using a modem.

In general, the payment host 140 is structured and arranged to transfer financial resources between different accounts. Typically, the payment host 140 maintains and manages one or more account associated with a health care consumer. Accounts associated with a health care consumer include, but are not limited to, personal accounts (e.g., checking, savings, line of credit) and accounts of a third party (e.g., employer, insurer) associated with the health care consumer. In some implementations, a financial institution (e.g., bank, investment firm, credit card company) operates the payment host 140. For example, a the payment host 140 may be operated by a financial institution in which the health care consumer has an account and/or a financial institution in which the employer of a health care consumer has an account. In other implementations, the payment host 140 may be operated by a resource provider (e.g., an employer), the health care intermediary 150, an insurance company, an alliance of health care providers or any other entity capable of managing and transferring funds between accounts.

Transferring financial resources may include having the payment host 140 access a bank account, a credit card account, or a credit line. For example, the payment host 140 may debit the account of the health care consumer and credit the account of a health care provider. Implementations also may include having the payment host 140 access a proxy account, a common account or a joint account. For example, the payment host 140 may initially debit a proxy account before a primary payment account is debited. In another example, the payment host 140 may debit an insurer's account for a portion of a transaction and debit a consumer's personal account for the remaining portion of the transaction. Typically, the payment host 140 may include one or more computing devices to manage these resources.

In one implementation, the payment host 140 maintains a primary account containing financial resources and a proxy account dedicated for reimbursing heath care providers for health care expenses. The proxy account may be a zero balance account for facilitating the transfer of funds between the primary account and a health care provider. For example, when a heath care expense is incurred, funds in an amount equal to the health care expense may be transferred from a primary account and held temporarily in the proxy account. The proxy fund then may be accessed by a health care provider or by a health care intermediary 150 to reimburse the health care provider.

Implementations of the payment host 140 may include a deployed account processor that enables access to account information. For example, a Pharmacy Benefits Manager ("PBM") may deploy a card reader with pharmacies. A pharmacist may swipe a PBM card to determine account information. Using the PBM card may not necessarily transfer resources. Rather, the deployed account processor may be used to provide the health care provider 120 with account information.

The health care intermediary 150 is a system structured and arranged to coordinate health care expenditures and resource allocation. In general, the health care intermediary 150 acts as an online health care account administrator or facilitator. An online health account is an online offering that enables a health care consumer to manage a health care program and expenditures in an online manner. Typically, the health care intermediary 150 is structured and arranged to coordinate reimbursement between a health care provider and a health care consumer. In general, the health care intermediary 150 is capable of processing transaction parameters related to health care products and services that have been or will be provided to the health care consumer. For example, a health care provider may provide claim-related information required to receive reimbursement for treating a health care consumer.

In one implementation, the health care intermediary 150 includes a security host 1520, a storage host 1522, a processing host 1524, a service host 1526, and an electronic funds transfer ("EFT") host 1528 in communication with each other. In general, each of the hosts may be independently or collectively implemented by a general-purpose computer capable of responding to and executing instructions in a defined manner. Examples of the hosts may include a personal computer, a special purpose computer, a workstation, a server, a device, a component, or other equipment or devices capable of responding to and executing instructions. Hosts may be arranged to receive instructions from one or more of a software application, a program, a piece of code, a device, a computer, a computer system or a combination thereof, which independently or collectively directs operations, as described herein. The instructions may be embodied permanently or temporarily in any type of machine, component, storage medium, or propagated signal that is capable of being delivered to hosts.

The security host 1520 is structured and arranged to verify identification and transaction information that is transmitted and received. Generally, the security host 1520 verifies the identity of users and systems that are communicating with the health care intermediary 150. The security host 1520 also may verify transaction parameters that are transmitted and received.

The storage host 1522 is structured and arranged to maintain data on one or more health care consumers who are participating in a health care program managed by the health care intermediary 150. The data in the storage host 1522 may include information about the identity and account information of the health care consumer. The information in the storage host 1522 also may include information related to various health care plans (e.g., repricing options) and program factors (e.g., additional insurance, additional indicators that may adjust the cost) as well as information about relationships with one or more health care providers.

The processing host 1524 is structured and arranged to coordinate allocation of resources for health care that has been or will be provided to a heath care consumer. Generally, the processing host 1524 will request, gather and receive transaction parameters from the client system 110, the HCP system 120, the payment host 140 and other hosts in the health care intermediary 150. The processing host 1524 enables a transaction to be completed based on received transaction parameters. The processing host 1524 also may track health care expenses and notify a health care consumer of completed and/or pending transactions. Generally, the processing host 1524 will display a user interface (e.g., Web page) and/or send a notification message to the client system 110. The user interface may include any type of content (e.g., text, graphics, audio, video) and the notification message may include any type of communication (e.g., e-mail message, instant message, voicemail, alarm) capable of being rendered by the client system 110.

The services host 1526 is structured and arranged to offer one or more services databases to the health care consumer. Generally, the services host 1526 is structured and arranged to enable a health care consumer to search through a directory of information and generate results most relevant to the search parameters. Examples of the services host 1526 may include a directory of health care providers and the ability to search for a health care provider by location, by costs, by affiliation and/or by specialty. Implementations of a services host 1526 also may include various health monitoring programs and assessments that enable a health care consumer to proactively manage health care by tracking lifestyle and regimens. For example, the services host 1526 may prompt a health care consumer for various information related to age, profession and gender. With this information, the services host 1526 may remind the health care consumer to schedule various check-ups.

The EFT host 1528 is structured and arranged to coordinate an electronic funds transfer. Generally, the EFT host 1528 accesses and appropriately debits and credits accounts associated with a health care provider and a health care consumer. For example, the EFT host 1528 may direct the transfer of funds from an account maintained by the payment host 140 to an account associated with a health care provider. In some implementations, the EFT 1528 host directs funds to be paid from a personal account (e.g., bank account, credit card account) of the health care consumer in situations where the health care consumer is financially responsible and must pay out-of-pocket for heath care expenses. In other implementations, the EFT host 1528 directs funds to be paid from an account of a third party (e.g., employer, insurer) associated with the heath care consumer in situations where the third party is financially responsible for the health care expenses of the health care consumer.

Figure 2:
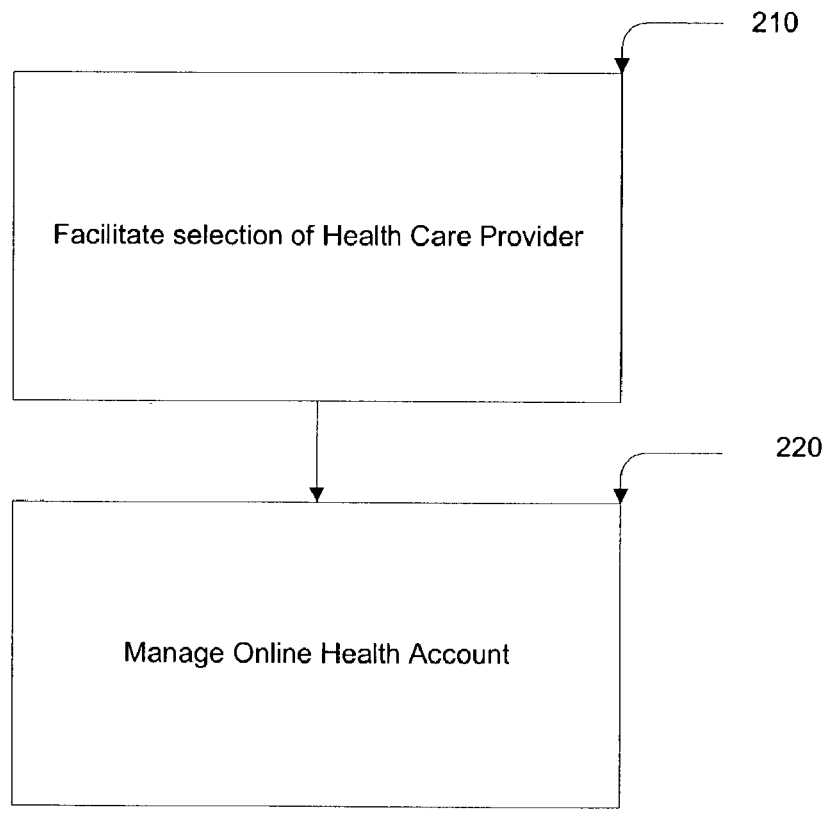
FIG. 2 is a flow chart depicting the operation of a health care intermediary in a health care system.

Referring to FIG. 2, the computer system 100 operates according to a procedure 200. The procedure 200 generally involves facilitating selection of a health care provider (step 210), and managing an online health account (step 220). The procedure 200 may be implemented by any suitable type of hardware (e.g., device, computer, computer system, equipment, component); software (e.g., program, application, instructions, code); storage medium (e.g., disk, external memory, internal memory, propagated signal); or combination thereof. Typically, the health care intermediary 150 will perform the procedure 200. However, other implementations may involve performing some aspects of the procedure 200 on one or more other systems, such as the client system 110 shown in FIG. 1.

Initially, the health care intermediary 150 facilitates selection of a health care provider (step 210). In general, facilitating selection of a health care provider includes presenting information about a health care opportunity to a health care consumer. Typically, presenting information includes enabling a health care consumer to view information on a client system 110 by, for example, using a web browser on a personal computer. Generally, a health care opportunity is a prospect of receiving health care from a health care provider. A health care opportunity describes a spectrum of possibilities for receiving health care. For example, a health care opportunity may include an appointment with a specified physician at a specified time and location. However, a health care opportunity does not require a high level of specificity. For example, a health care opportunity may only include contact information for a health care provider. Implementations of a health care opportunity may include an indication that a procedure should be performed annually. For example, a health care consumer participating in a monitoring program may receive a reminder to schedule a checkup to be performed annually.

Typically, facilitating selection of a health care provider includes manipulating information in a database of health care providers and health care opportunities to present a data set of results that are responsive to the priority expressed by the health care consumer. In one example, a health care consumer designates cost as a determining criterion. As a result, the health care opportunities displayed are ranked according to cost. In another example, a health care consumer prioritizing location would be presented with health care opportunities that reflect this prioritization (e.g., in a specified geographic region, within five miles). Typically, implementations reflect multiple prioritizations. For example, a health care consumer may wish to see a certain type of physician (e.g., pediatrician) in a certain location (e.g., less than five miles) and below a certain cost (e.g., $50).

In some implementations, facilitating selection of a health care provider may include a gateway step that enables a health care consumer to select a health care opportunity. In one implementation, the contact information of a physician is displayed so that a health care consumer may dial the phone number to schedule an appointment. Implementations may feature an integrated manner of selecting a health care opportunity. For example, a display of health care provider information may include displaying an electronic link (e.g., hyperlink, messaging link) in a web browser. Clicking on the electronic link may generate a message that is transmitted to the health care provider and solicits appointment availability. Other implementations may enable a health care consumer to actually select the health care opportunity. For example, a schedule of availability may be displayed to enable a health care consumer to click on a block of time to schedule an appointment.

With a health care provider selected (either as part of step 210 or through other means), the health care intermediary 150 manages an online health account to manage health care resources (step 220). Generally, an online health account enables a health care consumer to compensate or reimburse a health care provider for health care products and services that have been or will be provided. Managing an online health account includes the process by which a health care consumer reimburses a health care provider in addition to the administrative steps of establishing, configuring, modifying and terminating the online health account.

Figure 3:
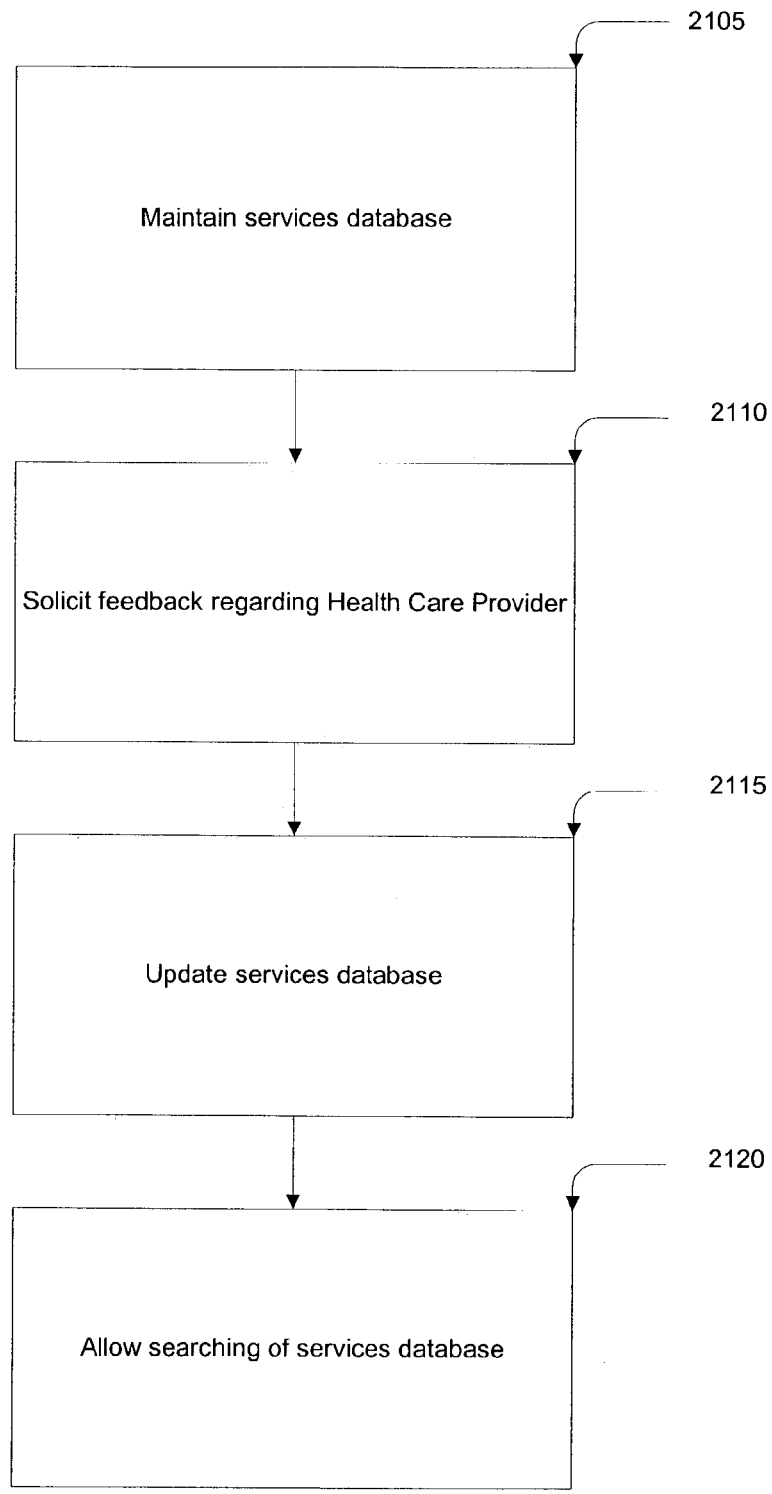
FIG. 3 is a flow chart illustrating one method of facilitating the selection of a health care provider.

FIG. 3 illustrates one method of facilitating selection of a health care provider (e.g., step 210). The procedure in FIG. 3 may be implemented by any suitable type of hardware (e.g., device, computer, computer system, equipment, component), software (e.g., program, application, instructions, code), storage medium (e.g., disk, external memory, internal memory, propagated signal), or combination thereof. Although FIG. 3 is typically performed on a health care intermediary 150, aspects may be performed on the other devices in the health care system 100. For example, portions of facilitating selection of a health care provider may be performed by a client system 110 associated with a health care consumer.

Facilitating selection of a health care provider generally involves operating a services database and enabling a health care consumer to identify health care opportunities in accordance with preferences and priorities designated by the health care consumer. Facilitating selection of a health care provider includes maintaining a services database (step 2105), soliciting feedback regarding the health care provider (step 2110), updating the services database (step 2115), and allowing a search of the health care provider database (step 2120).

Initially, the health care intermediary maintains a services database (step 2105). Maintaining a services database generally includes operating a database of health care related information and making it accessible to health care consumers. For example, maintaining a services database may include operating a web server and making it accessible to health care consumers across the Internet. The services database generally resides with the health care intermediary 150. Implementations may include distributing the services database across more than one entity. For example, aspects of the services database describing appointment availability may reside with the health care provider whose services are being offered. In another example, the health care intermediary 150 may incorporate information from a content provider and repackage the information with supplementary information.

As part of maintaining quality assessments in the services database, the health care intermediary 150 may solicit feedback regarding the health care provider (step 2110). For example, the health care intermediary 150 may question a health care consumer as to the timeliness of service, and the quality of health care provided.

Generally, soliciting feedback begins with a health care consumer receiving a solicitation. Implementations may include having the health care consumer receive a web form to be filled out and submitted. Implementations also may include having the health care consumer receive an electronic mail message or an automated telephone call, or having a proprietary application solicit feedback.

The health care consumer provides feedback. For example, the health care consumer may fill out a web form or respond to another of the types feedback solicitation described above. The health care intermediary receives the feedback and transmits updated information based on the received feedback to the services database. In this manner, those examining the record of a health care provider may subsequently view scores and comments provided by the health care consumer.

In order to present the health care consumer with accurate and timely information, the health care intermediary 150 updates the services database (step 2115). Updating the services database generally includes ensuring that the information in the services database reflects the most current information. Typically, updating the services database involves transmitting current information to the services database in an automated manner. The automated manner may include transmitting a datagram, an electronic mail message, a web page submission, or a submission by a proprietary application. For example, the services database may be synchronized with a database of a health care provider (e.g., hospital). Implementations of updating the services database may include validating, summarizing and/or or correlating the data before the data is added to the services database. For example, feedback scores of a health care provider may incorporate numerical scores and ratings in an overall average score. In another example, the comments may be summarized, filtered or validated before the comments are posted in the services database.

Updating the services database also may include having the health care intermediary 150 integrate information provided by the health care consumer with other information. For example, a health care consumer may access a provider database in the services host 1526 to select a physician. The services host 1526 may not have pricing information available about the cost of the physician. After the health care consumer is treated by the physician and reimburses the physician for the health care provided from an online account, the health care intermediary 150 may integrate the information about the cost of the transaction into the services host 1526. Subsequent access to the services host 1526 by a health care consumer includes the cost of the transaction. In another example, a health care consumer may access the services database to select a physician. The health care intermediary 150 may associate that physician with the profile of the health care consumer so that subsequent searches will display previously selected health care providers.

Updating the services database also may include enabling content be available based on information describing a health care transaction. For example, a health care intermediary may process a transaction for a patient seeing a cardiologist. With this information, the health care intermediary 150 may enable access to news articles relating to cardiovascular health and/or transmit them to the patient. In another example, the patient may receive an online prompt or message inquiring if the patient wishes to participate in an online cardiovascular workbook designed to monitor and improve cardiovascular health. Other examples may include a situation in which processing a transaction to purchase a migraine medication enrolls the patient to receive a migraine news articles.

The health care intermediary 150 allows the health care consumer to search the services database (step 2120). Searching generally includes attempting to identify health care providers that meet the criteria of the health care consumer. For example, a health care consumer may search for a health care provider by examining the quality assessments of patients that have visited the health care provider and provided feedback, such as the feedback provided in step 2110. In another example, the health care consumer may search for a health care provider that participates in an affiliated network offering more desirable pricing plans (e.g., better co-pay pricing). Other examples of services mentioned above include searching based on geographic proximity and price.

The health care intermediary 150 may augment the search with information from other sources (e.g., billing information, customer profile information). For example, the health care intermediary 150 may include search parameters with information relating to participation in discount pricing plans.

The health care consumer receives the results and may display all or part of the results. Implementations may include downloading a portion of the database to a local communications device (e.g., client device 112) and searching the local database before searching a larger network database.

Figure 4:
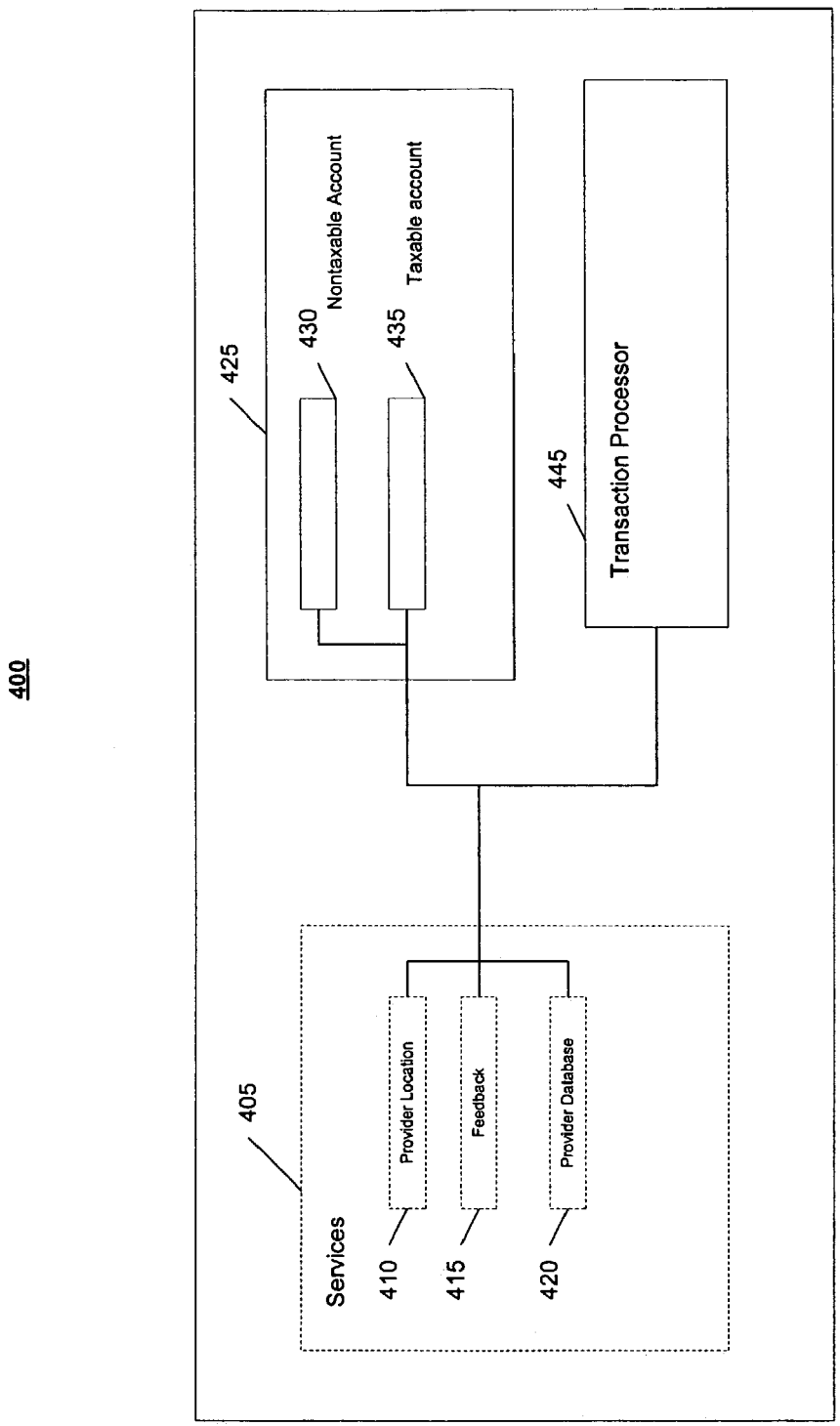
FIG. 4 is an exemplary block diagram of an online health care account that enables a health care consumer to manage health care decisions and expenditures.

Referring to FIG. 4, the health care intermediary 150 may act as an administrator for an Online Health Account 400. The OHA ("Online Health Account") 400 is an online service offering administered by the health care intermediary 150. The OHA 400 is structured and arranged to act as an online controller that enables a health care consumer to allocate health care resources (e.g., money, credit) and electronically reimburse a health care provider. The OHA 400 generally includes a services database 405, a HSA ("Health Savings Account") 425, and a transaction processor 445.

The services database 405 may be structured and arranged to include one or more services and to allow the health care consumer to integrate expending resources with one or more services. Services database 405 typically includes a location database 410, a feedback database 415, and a provider database 420 that enable a health care consumer to search one or more databases to assist with their health care needs. For example, one implementation may allow a health care consumer to search a provider database 420 and identify a health care provider that meets criteria specified by the health care consumer. In another example, the OHA 400 may enable the health care consumer to identify one or more health care providers in a specified geographic radius by examining a provider location database 410. In another example, the OHA 400 may allow the health care consumer to identify a health care provider based on cost criteria (not shown). Identifying a health care provider may enable a health care consumer to create a health care opportunity (e.g., an appointment).

The HSA 425 may be structured and arranged to enable a health care consumer to compensate a health care provider for services provided. The HSA 425 may include resources provided by one or more resource providers (e.g., employer, insurer) and/or the health care consumer. In one implementation, the HSA 425 is a nontaxable account dedicated for payment of health care expenses using pretax funds. For example, an employer may offer a HSA as part of an employee's compensation package and agree to allocate a fixed amount of funds to the HSA. Typically, the employer will periodically allocate HSA funds for each similarly situated employee and carry balances forward so that an employee's HSA will grow over time. The HSA may contain actual funds or indicate an amount of credit available to an employee.

Funds or credits in the HSA are designated for payment of qualified health care expenses, and the HSA is designed so that payment may be made to a health care provider at the time of service. In one implementation, an employer may set up a proxy account (e.g., a zero balance account) specifically designated for payment of employee health care expenses. When the employer is notified of a claim, the employer transfers funds in amount equal to the claim from a primary account to the proxy account. The funds then are transferred from the proxy account to the health care provider. As funds are transferred to a health care provider from the proxy account, the HSA is debited and a running total of distributions are maintained.

Implementations also may include allowing the health care consumer to pay for health care directly from the HSA 425. For example, a patient may provide a magnetic card with HSA 425 information enabling a physician to debit the HSA 425 for services provided.

In some implementations, the HSA 425 may include a nontaxable account and a taxable account. For example, the nontaxable account may include funds or credits that are allocated on a pretax basis and used as the primary resource for paying health care expenses. The taxable account may include supplemental funds that are above a pretax threshold and allocated to pay health care expenses. In some cases, health care consumers may be able to withdraw or allocate funds in the taxable account for non-health care purposes.

In other implementations, aspects of a HSA 425 may be associated with a FSA ("Flexible Savings Account"). For example, a health care consumer spending medical resources may be given the choice of accessing the FSA or the HSA 425 to pay for medical expenses.

The OHA 400 may include one or more transaction processors 445 structured and arranged to process transactions for health care that has been provided. Generally, the transaction processor 445 may be used to receive a transaction (e.g., a charge, a bill, a claim) and associate the transaction with one or more parameters from the health care consumer. For example, the transaction processor 445 may receive the charge and wait for the health care consumer to acknowledge the charge.

Figure 5:
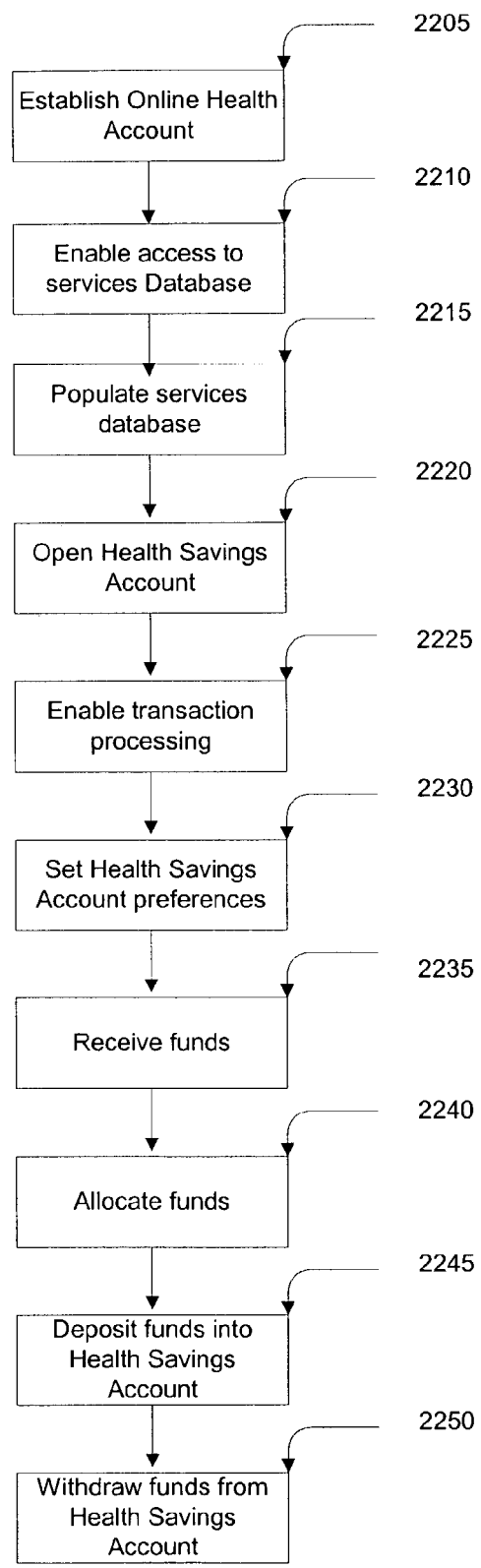
FIG. 5 is a flow chart depicting one operation of an online health care account.

FIG. 5 illustrates one method of enabling a health care consumer to manage an OHA 400 (e.g., step 200). The procedure in FIG. 5 may be implemented by any suitable type of hardware (e.g., device, computer, computer system, equipment, component), software (e.g., program, application, instructions, code), storage medium (e.g., disk, external memory, internal memory, propagated signal), or combination thereof.

Although FIG. 5 generally describes operating an OHA 400 on a health care intermediary 150, aspects may be implemented on other hosts in the health care system 100. For example, the health care intermediary 150 may direct expenditures and withdrawals of an account residing on payment host 140.

Initially, the health care intermediary 150 establishes an OHA 400 for the health care consumer (step 2205). Generally, establishing the OHA 400 includes enabling access to a unique online account that enables the health care consumer to receive various services and to compensate a health care provider for provided health care.

Typically, establishing an online health account includes registering a health care consumer with the health care intermediary 150. Examples of registering include completing an application to create an OHA 400 or transferring an existing OHA 400 to the health care intermediary 150. Paper and/or electronic means may be used to register. For example, a health care consumer may receive the forms with instructions for registering electronically. Another example may include a portion of the registration that is filled out electronically, then printed, signed and mailed.

As part of establishing an OHA 400, the health care intermediary 150 enables access to one or more services database through the OHA 400 (step 2210). Implementations of enabling access may include enabling access to standard and/or premium services. For example, as part of registering with a health care intermediary 150, a health care consumer may receive access to content about a set of services, while the health care intermediary 150 may require an additional fee for access to content about certain services. Implementations also may include enabling access to personalized content. For example, content may be personalized to a region, gender, interest or demographic. Based on this personalization, the health care consumer may enroll in a health care program designed to proactively manage health care. Proactively managing health care includes participating in checkups and tracking lifestyle information with the goal of minimizing medical problems by detecting any conditions or risk factors at an early stage.

To create content to be accessed by health care consumers, the health care intermediary 150 populates the services database (step 2215). Typically, this involves registering one or more partners to provide the health care intermediary 150 with content to be accessed (e.g., a services database for the health care consumer to search for a health care provider). For example, a partner may complete a licensing agreement to register with the health care intermediary 150.

Implementations may include allowing either the health care intermediary 150 or the partner to establish a relationship in one or several steps. For example, the health care intermediary 150 may initiate the operation while the registration may include several steps to provide and verify the content.

Once registered, the partner provides content for the services database to the health care intermediary 150 (e.g., services host 1526). Providing content may include providing content directly to the health care intermediary 150 or enabling access to content residing with the partner. For example, a health care consumer accessing the OHA 400 may be dynamically linked in a web page.

In some implementations, the health care intermediary 150 may integrate content from disparate sources. For example, the health care intermediary 150 may combine data from the health care provider with data from a partner. In another example, the health care intermediary 150 may combine information from multiple partners to create a composite of information from multiple sources. This composite may be displayed to the health care consumer to enable a view of information that was not previously linked or accessible on the same display. In a detailed display of health care provider information, the display may feature data and links with location information, contact information, cost data, Health Care Financing Administration data, tax data, and licensing information (e.g., sanctions). Integration may include combining OHA 400 information with the services database. For example, accessing the services database from an OHA 400 may automatically populate aspects of the services database with content specific to that particular health care consumer.

With the OHA 400 established, a HSA 425 is opened (step 2220). In one implementation, opening the HSA 425 includes establishing a nontaxable account enabled to send and receive resources. In other implementations, opening a HSA 425 includes establishing both a nontaxable account 430 and a taxable account 435 enabled to send and receive resources. The HSA 425 may include a logical partition on a larger pooled account or each account may be a separate and distinct financial entity.

With the HSA 425 opened, the health care intermediary 150 enables transaction processing for the health care consumer (step 2225). Generally, transaction processing describes the process by which a health care consumer can reimburse a health care provider for provided health care. Enabling a health care intermediary 150 to process a transaction includes enabling the health care consumer to receive health care, and enabling the health care intermediary 150 to exchange transaction parameters from other devices in the health care system 100.

With the OHA 400 enabled to process transactions, the health care intermediary 150 sets HSA preferences (step 2230). Generally, setting preferences for the HSA 425 determines the manner with which new resources are inserted and withdrawn. Implementations may allow the health care intermediary 150 or an employer to control preferences in allocating funds to the HSA 425.

The health care intermediary 150 receives funds in the HSA 425 (step 2235). Typically, receiving funds may include depositing funds according to the set preferences. Implementations may include placing additional resources in the HSA 425 periodically. For example, an employer may annually credit the HSA 425. In another example, the health care consumer may make monthly contributions into the HSA 425.

Receiving funds may include having the health care consumer receive an indication of the new influx of resources. For example, when the health care consumer accesses the OHA 400, a message may be displayed to indicate that the account has been credited. This indication may include the date and amount of the credit. In another example, the health care consumer may receive an electronic mail message indicating that there has been or will be an influx of new resources into the HSA 425.

The health care consumer allocates funds to reimburse a health care provider for a health care transaction (step 2240). Typically, a health care transaction includes selecting health care, receiving health care, and reimbursing for provided health care.

Initially, a health care consumer initiates a health care transaction by selecting a health care provider to provide health care. Selecting a health care provider may be accomplished independently or based on the results of searching the services database (e.g., step 210 and/or step 2120). Selecting a health care provider may include having the health care consumer contact the health care provider by automated means (e.g., an instant message, an email, use of a proprietary application, or a transmittal of information from a web front end), a telephone call, or directly visiting the health care provider to receive health care.

Regardless of the manner in which the health care provider is selected, the health care consumer receives health care. Receiving health care generally corresponds to the health care offerings (e.g., physician services, therapy, hospital support, pharmaceuticals) described above.

After the health care has been provided, reimbursement for provided health care is initiated. Initiating the health care reimbursement may include providing a credit or debit card that debits an account (e.g., HSA, proxy account, company account, credit card account, bank account). In one example, the health care consumer provides a proprietary card of the health care intermediary 150 to a card reader. In another example, the health care consumer provides a "smart" card that includes the ability to provide or direct resources for reimbursement. In another example, the health care provider uses a computing device (e.g., HCP device 122) to initiate reimbursement proceedings. For example, the health care provider may access a web site administered by the health care intermediary 150 to initiate the health care reimbursement. Implementations also may include initiating or providing reimbursement in advance of receiving health care.

With the reimbursement initiated, the health care intermediary 150 receives the reimbursement request. Generally, the health care intermediary 150 receives the reimbursement request in the format described above. However, implementations may include receiving the reimbursement request in a manner different than that used in initiating the health care reimbursement. For example, the health care consumer may initiate the reimbursement by providing a credit card, and the health care intermediary 150 may receive an electronic summary of the transaction from the credit card provider (e.g., payment host 140).

To complete the transaction, the health care consumer may need to acknowledge or authorize a transaction. For example, the health care consumer may be directed to complete a web form acknowledging the health care received.

In completing a transaction, the health care intermediary 150 may generate a display of the adjusted account. For example, when the health care consumer uses a web browser and next accesses the OHA 400, the web browser may display the adjusted account. Implementations may include generating a marker indicating that an adjustment has been made or should be made.

Allocating resources is not limited to automated means. Implementations may include using non-automated means to access a HSA 425. For example, a health care provider may file a claim through a claims processing center to receive reimbursement. The claims processing center adjusts the HSA 425 and reimburses the health care provider. In another example, a health care consumer receives a monthly statement by mail documenting the HSA 425 and the transaction. The health care consumer would complete the enclosed paperwork to process a health care transaction. Other examples may include having a health care consumer use a telephone to access account information through a phone menu system.

The health care intermediary 150 enables resources to be deposited in the HSA 425 (step 2245). Generally, depositing funds in the HSA 425 (step 2245) is related to the process of inserting resources into the nontaxable account 430 or the taxable account 435, while receiving funds (step 2235) is related to the process of receiving and depositing additional resources into the HSA 425. In one example of depositing funds, the health care intermediary 150 deposits $1,000 into the nontaxable account and $1,000 into a taxable account after receiving $2,000 in funds (e.g., step 2235). Implementations may include having the health care intermediary 150 direct a payment host 140 to transfer funds between different accounts. For example, the payment host 140 may transfer funds from an employer account to the HSA 425.

The health care consumer may be allowed to withdraw funds (step 2250). Typically, with the health care consumer controlling the expenditures from the HSA 425 and the possibility of receiving unallocated funds from the taxable account, it is expected that health care consumers will prudently manage their health care resources with the expectation that the taxable account becomes an investment vehicle. In general, the health care consumer makes a request to withdraw resources. The request to withdraw may be implemented by an electronic mail message, a web submission, and/or non-automated techniques (e.g., paper form submission, person-person communication).

Before enabling the withdrawal, the health care intermediary 150 settles pending transactions. This typically includes completing all transactions and debiting the HSA 425 to reimburse health care providers for health care provided. For example, the health care intermediary 150 may receive the request to withdraw funds and determine that several transactions for reimbursement have not been completed and the health care providers have not been compensated. Implementations may include waiting for a certain time to elapse to ensure that there are no pending transactions that may not be reimbursed before the withdrawal.

Once pending transactions have been completed, the health care intermediary 150 may complete withdrawing funds by transferring resources to the health care consumer. Implementations of transferring resources may include directing a payment host 140 to transfer funds to a different account. In one example, the health care intermediary 150 may create a check payable to the health care consumer. Implementations may include having the health care intermediary 150 direct a third party to transfer the resources. For example, the health care intermediary 150 may direct a bank to transfer funds to the health care consumer.

Finally, the health care consumer receives the withdrawn resources. Typically, this involves receiving the resources in the manner of the withdrawal.

Figure 6:
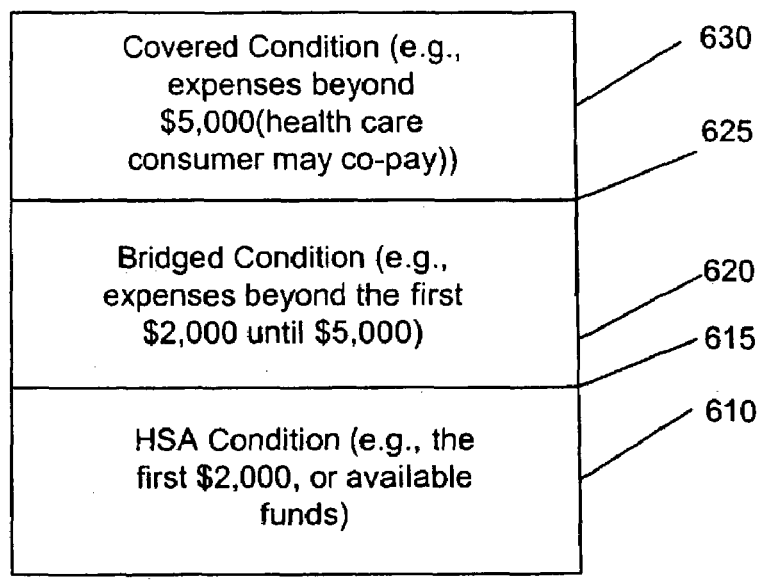
FIG. 6 is a flow chart depicting one implementation of operating a health savings account.

FIG. 6 shows one implementation of a health account structure 600 for managing, allocating, and distributing health care funds. In general, the health account structure 600 is configured to manage funds received from resource providers (e.g., employers) and to distribute the funds in response to payment requests from health care providers (e.g., doctors, pharmacists) for qualified health care expenses (e.g., treatment, medication). The health account structure 600 typically includes several operating conditions for managing the distribution of funds. For example, the health account structure 600 includes a Health Savings Account ("HSA") condition 610, a bridged condition 620, and a covered condition 630.

The HSA condition 610 corresponds to a situation in which funds from a HSA are available for distribution as payment for incurred or prospective medical expenses. For example, an employer may offer a HSA as part of an employee's compensation package. In one implementation, an employer may agree to allocate a fixed amount of funds to a HSA for each similarly situated employee. Typically, the employer will allocate HSA funds periodically and carry balances forward so that an employee's HSA will grow over time. The HSA may contain actual funds or indicate an amount of credit available to an employee.

Funds or credits in the HSA are designated for payment of qualified health care expenses, and the HSA is designed so that payment may be made to a medical care provider at the time of service. In one implementation, an employer may set up a payment account (e.g., a zero balance account) specifically designated for payment of employee health care expenses. When the employer is notified of a claim, the employer transfers funds in an amount equal to the claim from a general account to the payment account. The funds then are transferred from the payment account to the health care provider. As funds are transferred to a health care provider, the HSA is debited and a running total of distributions is maintained.

The HSA may be managed by the employer and/or by a health care intermediary. For example, the health care intermediary may provide an interface among employers, employees, and health care providers. In one implementation, the health care intermediary is configured to provide updated HSA information to health care consumers (e.g., employees) and resource providers (e.g., employers) through the Internet. The health care intermediary also may be configured to receive claims submitted from a health care provider, confirm or inform the health care provider that payment is to be made from a HSA, notify the employer of a claim amount, and transfer funds from an employer's payment account to the health care provider. More details regarding managing a HSA are described in U.S. patent application Ser. No. 09/924,952 filed Aug. 9, 2001, which is incorporated by reference in its entirety.

The HSA condition 610 is in effect up to a bridged threshold 615. In general, the bridged threshold 615 reflects the fluctuating balance of a HSA. The bridged threshold 615 initially is set by the resource provider and then fluctuates over time. For example, an employer may offer to allocate a lump sum of $2,000.00 per year to an employee's HSA, thus initially setting the bridged threshold 615 at $2,000.00. The bridged threshold 615 fluctuates as the employer makes future periodic allocations and the employee makes deductions for health care expenses. The HSA condition 610 is in effect as long as the amount of total distributions for health care expenses is below the bridged threshold 615. That is, HSA funds may be distributed to pay for health care expenses up to the bridged threshold 615. Once the bridged threshold 615 is reached and/or exceeded, the HSA condition 615 ceases and the bridged condition 620 begins.

The bridged condition 620 corresponds to a situation in which HSA funds have been exhausted. In general, health care consumers will bear financial responsibility for health care expenses incurred when the bridged condition 620 is in effect. For example, an employee may have a deductible ceiling (e.g., bridged threshold 615) in a HSA, that when reached, alleviates the employer from financial responsibility. That is, the employee must pay "out-of pocket" for health care expenses above and beyond which the employer has agreed to pay through a HSA.

The bridged condition 620 also may arise when a health care consumer is a new employee with limited resources in the HSA. For example, if an employer makes monthly allocations to an employee's HSA, the HSA may be inadequate to cover a significant health care expense incurred shortly after an employee begins work. Once the allocated HSA funds have been exhausted, the bridged condition 620 applies and the health care consumer must pay for his or her health care expenses.

In one implementation, a health care intermediary notifies health care consumers and/or medical providers that the bridged condition 620 is in effect. Notification may be triggered when health care expenses meet or exceed the bridged threshold 615 or some other triggering amount approaching the bridged threshold 615. For example, the health care intermediary may notify a health care provider when the health care provider submits a claim for medical expenses. The health care intermediary also may notify a health care consumer that health care expenses are approaching the bridged threshold 615 and remind the health care consumer that future medical expenses may need to be paid out-of-pocket. Notification may occur in writing, by telephone, by e-mail, or through a UI (e.g., Web page) having charts, figures, graphs, text, images, audio, video, and/or any other type of content.

Typically, out-of-pocket expenditures by health care consumers are tracked. Tracking may be performed by a health care intermediary and/or by a resource provider, for example. In one implementation, a health care intermediary tracks out-of-pocket expenditures and provides Internet-accessible updated information to health care consumers.

The bridged condition 620 is in effect up to a covered threshold 625. That is, the bridged condition 620 is in effect when the HSA is exhausted and the amount of total distributions for health care expenses is below the covered threshold 625. In general, the covered threshold 625 is the amount at which a resource provider (e.g., employer) resumes at least some financial responsibility for medical expenses. Typically, the resource provider sets the covered threshold 625 at a fixed amount for a given year.

The covered condition 630 corresponds to a situation in which a resource provider resumes a financial obligation for health care expenses. For example, in addition to allocating $2,000.00 per year to an employee's HSA, an employer also may offer to pay for a certain percentage (e.g., 80%, 100%) of health care expenses above $6,000.00 (e.g., covered threshold 625) incurred in a given year. Once the covered threshold 625 is reached and/or exceeded, the bridged condition 620 ceases and the covered condition 630 begins.

It should be noted that unlike the bridged threshold 615, the covered threshold 625 does not fluctuate as the employer makes future periodic allocations and the employee makes deductions for health care expenses during a given year. As such, in cases where the HSA balance exceeds the covered threshold 625, the covered threshold 625 is reached before the bridged threshold 615. In this scenario, health care consumers are able to bypass the bridged condition 620 and avoid substantial out-of-pocket expenses. This scenario demonstrates an important benefit of growing a HSA over time.

Furthermore, HSA funds above the covered threshold 625 may be used for co-payments when the health care consumer must pay for a percentage (e.g., 20%) of heath care expenses above the covered threshold 625. To illustrate, a health care consumer having a HSA balance of $7,000.00 and an employer that pays 80% of medical expenses over a $6,000.00 would pay nothing out-of-pocket and have a remaining HSA balance of $800.00 for a $7,000.00 health care expense.

In some implementations, the covered condition 630 may include tiers of coverage. For example, an employer may offer to pay 80% of health care expenses over $6,000.00 and 100% of health care expenses over $10,000.00. Accordingly, the heath account structure 600 may include one or more tier thresholds (not shown). Additionally, the covered condition 630 may include a catastrophic insurance condition under which the resource provider (e.g., employer) is indemnified by an insurance company for extremely high health care expenses (e.g., over $100,000.00).

Figure 7:
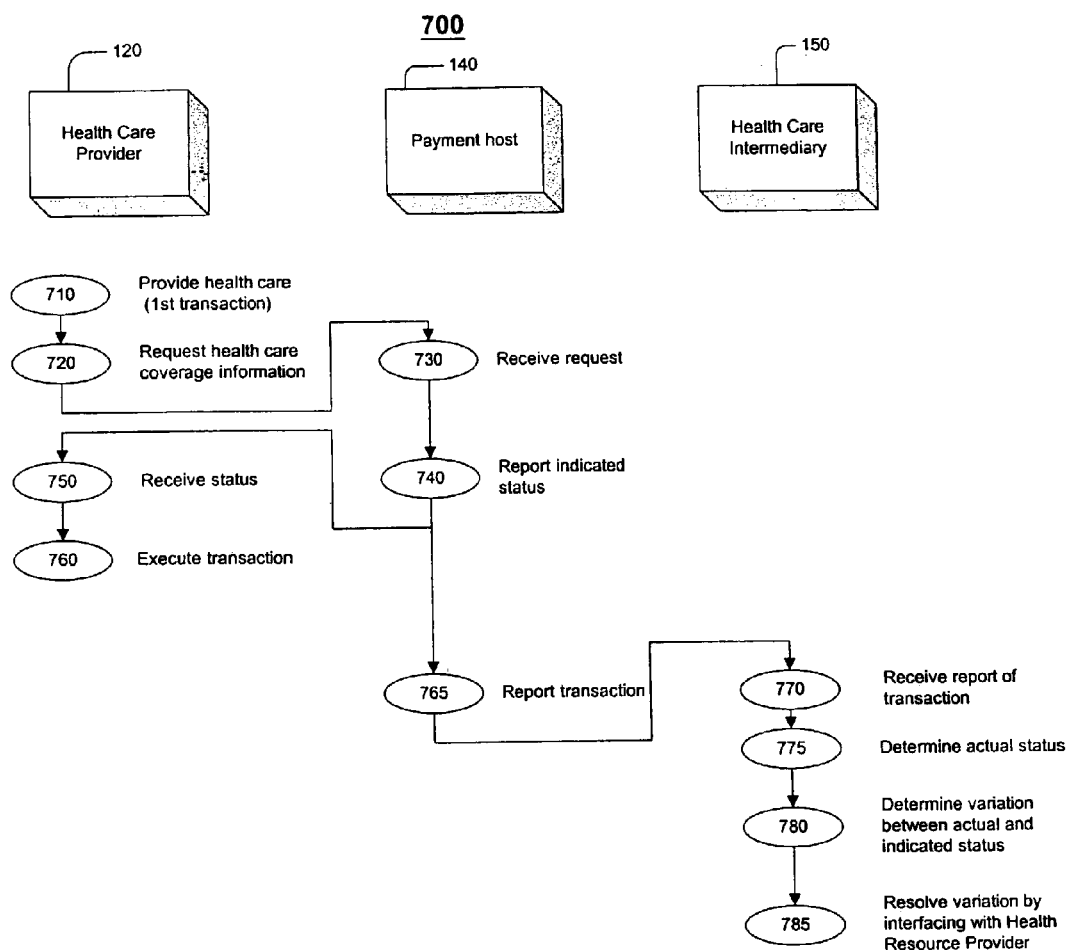
FIG. 7 is a flow chart illustrating one method of using the health savings account to provide and correct for variations that occur in the course of operating a health savings account.

FIG. 7 illustrates how the health account described in FIG. 6 may be operated when the health care provider initiates a transaction based on a dated indication for the status of the account. Typically, a health care provider will identify the status of the account before initiating a health care transaction to receive reimbursement. However, in some implementations, the indicated status information may not reflect the actual status of the account. For example, a health care provider may update a deployed account processor daily to provide account status information to the health care provider 120. Due to this daily update, the indicated status may not reflect the actual status of the health account where a transaction will cause the status of an account to change. In one example, the cost of a health care transaction may change the actual status of the account from being in a HSA condition to a bridged condition. The variation may be corrected in subsequent transactions, providing a seamless interface for health care providers initiating the transaction.

In FIG. 7, health care system 700 includes a health care provider 120, a payment host 140, and a health care intermediary 150. In general, aspects of the systems in health care system 700 are described above. However, health care system 700 illustrates how a health care intermediary 150 may correct a variation in a health care transaction, where the transaction is initiated based on an indicated status that is different from the actual status of the account. For example, a payment host 140 may tell the health care provider 120 that the account is in a HSA condition when the actual status of the account includes a bridged condition. Generally, this variation creates a deficit that is corrected in a subsequent transaction. For example, a later transaction may ask the health care consumer to pay a higher co-pay in the covered condition that offsets the amount of the deficit.

Generally, the health care provider 120 initially provides health care (step 710). Providing health care may include providing a variety of health care products and services that were described in FIGS. 1-6 of the parent application. The health care may include pharmacy, dental, and medical services. Although some health care plans include separate programs for different categories of benefits (e.g., dental, pharmacy, and optical plans), implementations may include a common health account that integrates allocation of resources for several categories from an integrated account.

To compensate the health care provider 120 for providing the health care, reimbursement proceedings are initiated. Typically, the reimbursement is initiated by requesting health care coverage information (step 720). Generally, requesting health coverage information includes determining the status of the HSA as described with respect to FIG. 6 (e.g., HSA condition, bridged condition, covered condition).

Typically, requesting health care coverage information includes having the health care provider 120 interface with a payment host 140 to determine the account status. For example, a health care consumer purchasing prescription drugs provides a pharmacist with a PBM card to initiate reimbursement proceedings. The pharmacist, acting as the health care provider 120, swipes the PBM card into the payment host 140 (e.g., a card reader for a PBM), and determines the indicated status of the account.

The payment host 140 receives the request (step 730). The payment host 140 maintains a database of accounts and provides the account information to authorized requesters. Typically, the payment host 140 receives a periodic update from health resource providers and/or health care intermediaries. These updates are incorporated into the database. However, because the updates may be periodic and not reflect the actual (e.g., real time) status maintained by the health care intermediary, the account status provided by the payment host 140 is referred to as an indicated status. For example, after a day of medical appointments with several transactions, the amount of resources allocated may actually have put the health savings account into a bridged condition. In one instance, the health savings account may have insufficient funds to pay for the cost of the transaction.

Upon receiving the request, the payment host 140 determines and reports the status of the account (step 740). Upon receiving the status (step 750), the health care provider 120 may execute the transaction (step 760). In this case, the health care provider 120 charges the HSA.

Although the transaction is described as charging the HSA, executing the transaction may include having the health care provider 120 file a claim with the health care intermediary, and having the health care intermediary 150 charge the HSA and subsequently reimburse the health care provider.

Regardless of the procedure used to initiate the transaction, the payment host 140 reports the transaction (step 765). Typically, reporting the transaction includes sending a summary of the transaction (e.g., account number, cost, description of services, Current Procedural Technology ("CPT") code) to the health care intermediary 150.

The health care intermediary 150 receives the report of the transaction (step 770) and determines the actual status of the account (step 775). In the current example, the HSA is in a bridged condition. Because the actual status of the account is different from the indicated status of the account upon which the transaction was initiated, the health care intermediary determines the variation between the actual and indicated status (step 780). Determining the variation may include determining the financial discrepancy between the costs that were assigned based on the indicated status, and the costs as they would be assigned based on the actual status. For example, a health care provider may charge $100 against a HSA based on the indicated account status indicating the account is in a HSA condition. However, the HSA may only have $50 in the account, creating a deficit of $50.

The health care intermediary 150 resolves the variation (step 785). In the example of the variation including a $50 deficit, the health care intermediary interfaces with the health resource provider (e.g., insurance company, employer) to correct the $50 variation. The health resource provider advances $50 to the health care intermediary on behalf of the health care consumer (e.g., employee), and the $50 deficit is carried forward against the HSA of the health care consumer.

Processing the first transaction may include using additional procedures to complete the transaction. For example, the health care consumer may be asked to verify the claim. In another example, where the health care provider 120 executes the transaction by filing a claim with the health care intermediary 150, the health care intermediary may process the claim and allocate resources to reimburse the health care provider. Processing the claim may include consolidating multiple claims with the same health care provider and consolidating the reimbursement.

In any event, the first transaction is completed with a variation associated with the HSA. In the ongoing example of FIG. 7, a deficit of $50 is carried forward. Generally, the variation is resolved by adjusting the allocation of resources in a subsequent transaction where the health care intermediary 150 would provide resources, that is, in the HSA or covered condition. The variation may also be corrected in a subsequent infusion into the HSA.

Figure 8:
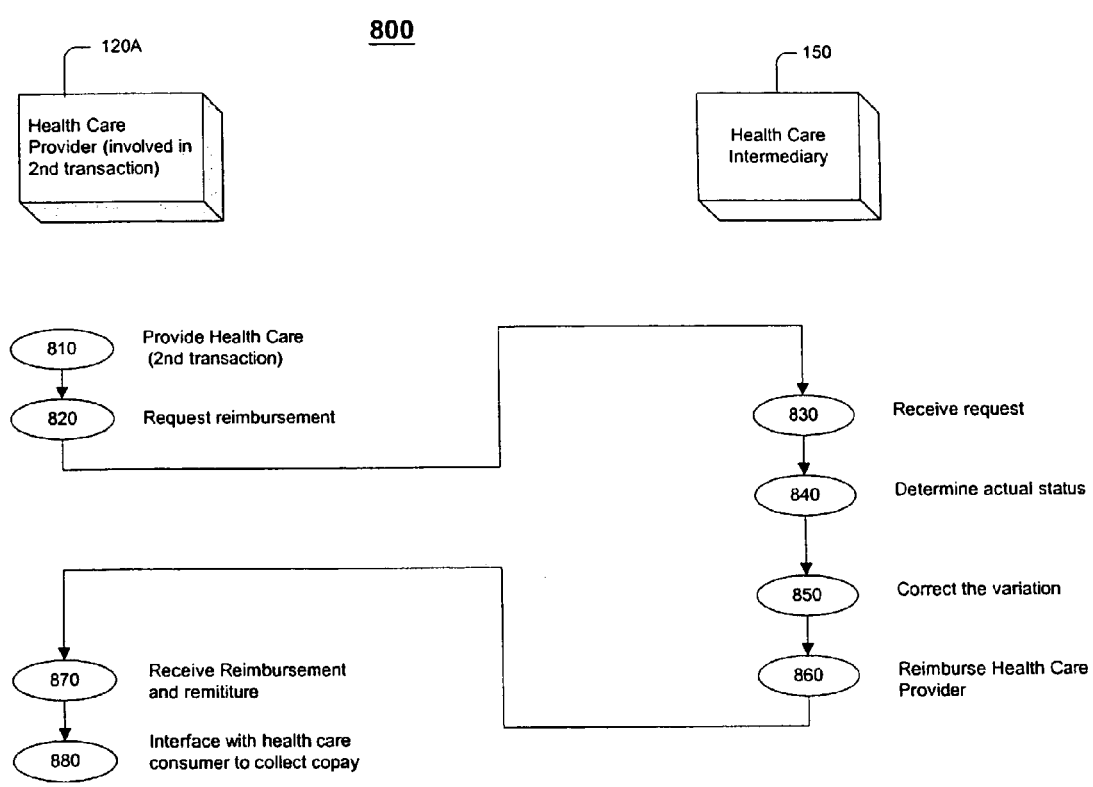
FIG. 8 is a flow chart illustrating one method of how a variation may be corrected in a second transaction that does not use a payment host.

To illustrate how a subsequent transaction can be processed to correct for a variation, FIG. 8 shows a second transaction that corrects for a variation previously created. In the example shown in FIG. 8, a payment host is not used to process the second transaction. For example, the second health care provider 120A may lack the infrastructure to use a payment host 140. Otherwise, the health care processing systems described with respect FIG. 8 are similar to the systems described with respect to FIG. 7. To illustrate how the variation may be corrected in a second transaction, the example of the $50 deficit described with respect to FIG. 7 will be used throughout the discussion of FIG. 8 to show an example of how the variation is corrected. However, correcting the variation in a second transaction is not limited to the described situation. Other forms of variations may be corrected as well, and the variations may be corrected through other techniques.

In any event, as part of the second transaction, the health care provider 120A provides health care (step 810). To receive reimbursement for the health care, the health care provider 120A initiates a reimbursement request (step 820). For example, a health care provider may file a claim with the health care intermediary.

The health care intermediary 150 receives the reimbursement request (step 830). For example, a medical claim form may be received. Upon receiving the transaction request, the health care intermediary determines the account status (step 840). In the continuing example, the HSA is in a covered condition with a variation for the $50 deficit that has been carried forward.

The variation is corrected, in this case, by offsetting the covered amount by the deficit (step 850). For example, in a transaction that costs $1,000 in the covered condition where the employer pays 80% of the costs in the covered condition, the health care intermediary may cause $750 be directed to the health care provider 120. The health care intermediary 150 then sends a remititure to the health care provider 120 to charge the health care consumer $250 (who is now without a $50 deficit in the HSA) (step 860). The health care provider 120 receives the reimbursement and remititure (step 870). The health care provider then interfaces with the health care consumer to receive the co-pay (step 880). At this point, the variation has been corrected.

Figure 9:
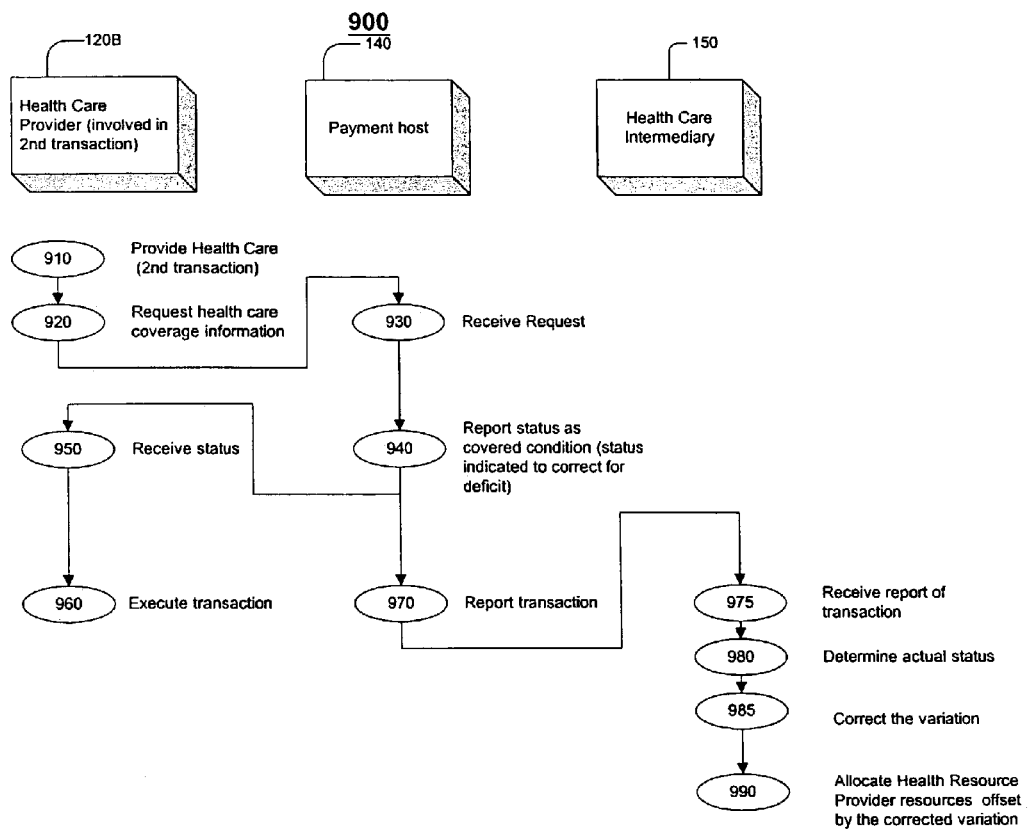
FIG. 9 is a flow chart illustrating one method of how a variation may be corrected in a second transaction that uses a payment host.

FIG. 9 illustrates how a second transaction that uses a payment host may be used to correct a variation. Health care system 900 includes a health care provider 120B, a payment host 140, and a health care intermediary 150. In general, aspects of the systems in health care system 900 are generally are similar to the systems described with respect to FIGS. 1-8. For example, both FIGS. 7 and 9 relate to processing a health care transaction through a payment host. Similarly, both FIGS. 8 and 9 relate to correcting a variation from a first health care transaction in a second health care transaction. However, FIG. 9 describes having the second health care transaction correct for the first health care transaction using the payment host.

Generally, the health care provider 120B initially provides health care (step 910). To compensate the health care provider 120 for providing the health care, reimbursement proceedings are initiated. Typically, the reimbursement is initiated by requesting health care coverage information (step 920). The payment host 140 receives the request (step 930).

Upon receiving the request, the payment host 140 determines the status of the account (not shown). The payment host 140 reports the indicated status of the account (step 940). Upon receiving the indicted status (step 950), the health care provider 120 may execute the transaction (step 960). In this case, the health care provider 120 charges the HSA the amount of any co-pay offset by the advanced amount. Thus, an account in a covered condition with an 80% co-pay, and a charge for $1,000 would charge a co-pay of $250 instead of $200.

Independent to the exchange between the health care provider 120B and the payment host 140, the payment host 140 reports the transaction (step 970). The health care intermediary 150 receives a report of the transaction (step 975). The report of the transaction is used to update the condition of the HSA. Upon receiving a report of the transaction, the actual status of the account is determined (step 980). In the current example, the HSA is in a covered condition and the account includes a variation in the form of a $50 deficit that has been carried forward. The health care intermediary 150 resolves the variation (step 985) and allocates resources based on the corrected variation (step 990). Thus, in the current example, the reimbursement to the health care provider 120B from the health care intermediary/health resource provider would be reduced $50, and the co-pay from the health care consumer to the health care provider would be increased by $50.

Other implementations are within the scope of the following claims. In particular, in some implementations, the health care consumer and payment host 140 may perform one or more functions described above as being performed by the health care intermediary 150. The health care consumer, health care provider, network, payment host, and health care intermediary also may be distributed across different entities in the health care system and may make use of one or more agents and/or proxies to perform certain functions.

Other examples of variations may include an account whose indicated status is a bridged condition, but crosses the bridged-condition threshold to make the actual status of the account a covered condition. Similar variations also may exist for a covered condition that moves into higher tiers of coverage. Variations are not limited to situations where the indicated status of the account reflects a status indicating fewer resources have been spent than actually been allocated. Variations may include having the indicated status show more resources being spent than have actually been spent and/or exist. For example, the payment host 140 (e.g., PBM device) may not indicate a subsequent infusion of funds. Thus, in one example, the PBM may indicate that insufficient funds exist, (e.g., a bridged condition) requiring the health care consumer to pay for the cost out-of-pocket, that is, the bridged condition. However, the HSA may have received an infusion that day. Another example of the indicated status showing more resources being spent than have actually been spent may include thresholds that are coupled to a calendar and/or periodic threshold. For example, updates to the payment host 140 may have an annual deductible threshold that occurs between the updates. Thus, the indicated status may not reflect the actual status because certain transactions in the previous period for the deductible no longer count against the deductible.

Although receiving reimbursement is shown as having occurred after the variation has been corrected, implementations may include receiving the reimbursement earlier. For example, reimbursement may be provided after the cost for the transaction is received by the health care intermediary 150. In this case, the resources are provided to the health care provider 120, and the variation is calculated afterwards. The operations have been described in the context of a health care system. However, these operations also could be used in the context of other transaction systems. For example, the operations could be performed in a benefit plan administered by a human resources department for a company, or in a transaction system administered by a financial institution.

What is claimed is:

1. A computer implemented method of administering a health saving account, the method comprising:

contracting by a benefits manager with or for the benefit of an employee to authorize the benefits manager to administer a health savings account for the employee;

contracting by the benefits manager with or for the benefit of the employee and an insurance company to authorize the benefits manager to administer a health insurance policy provided to the employee by the insurance company;

determining a deductible clause for the health insurance policy, wherein the terms of the deductible clause specifies financial responsibility for health expenses incurred by the employee, wherein any amount not responsible for by the health insurance policy would be charged to the employee;

contracting by the benefits manager with one or more health service providers to authorize the benefits manager to receive and adjust any health insurance policy payout prior to forwarding the adjusted payout to the one or more health service providers;

providing electronic communications between the benefits manager, the health insurance company, and the one or more health service providers by each entity having a computer, and the computers interconnected with a network;

in the benefits manager computer, maintaining a balance for the health savings account of the employee;

accepting, by the benefits manager, any contributions made on behalf of the employee and increasing the balance maintained in the benefits manager computer;

storing the deductible clause in the benefits manager computer;

one of the one or more health service providers computers sending a first request to the benefits manager computer over the network for reimbursement for first health services provided to the employee;

comparing, by the benefits manager computer, the first request for reimbursement with the deductible clause to determine financial responsibility for the first health services provided to the employee;

determining, by the benefits manager computer, that the employee is solely responsible for the first health services provided to the employee;

the benefits manager computer deducting the requested reimbursement from the employee's health savings account balance, wherein the resulting balance is negative;

the benefits manager computer transferring the deducted reimbursement to the health service provider computer making the first request to effect an electronic funds transfer therefor;

one of the one or more health service providers computer sending a second request to the benefits manager computer over the network for reimbursement for second health services provided to the employee;

comparing, by the benefits manager computer, the second request for reimbursement with the deductible clause to determine financial responsibility for the second health services provided to the employee;

determining, by the benefits manager computer, that the health insurance policy is responsible for covering at least a portion of the second health services provided to the employee;

the benefits manager computer receiving an electronic funds transfer from the insurance company computer to provide reimbursement for the covered portion;

the benefits manager computer deducting at least some of the outstanding negative balance from the amount for reimbursement to compensate for the employee's negative balance; and the benefits manager computer forwarding any remaining funds received from the insurance company computer to the health service provider computer making the second request to pay for the second health services rendered to the employee.

2. The method of claim 1, wherein a payment host computer is provided between the benefits manager computer and the one or more health service provider computers for processing payment transactions therebetween.

3. The method of claim 2, wherein the payment host computer comprises a Pharmacy Benefits Manager processor.

4. The method of claim 1, wherein the employee's negative balance is restored by a subsequent infusion into the health savings account.

5. The method of claim 1, wherein the health savings account integrates more than one benefit program.

6. The method of claim 1, wherein the health savings account is a tax favored account or not a tax favored account.

7. The method of claim 1, wherein the health savings account is not a tax favored account.

8. A computer program product for a computer implemented method of administering a health saving account, and including one or more computer readable instructions embedded on a tangible computer readable medium and configured to cause one or more computer processors to perform the steps comprising:

providing electronic communications between a benefits manager, a health insurance company, and one or more health service providers via respective computers interconnected over a network;

in the benefits manager computer, maintaining a balance for a health savings account of an employee;

accepting, by the benefits manager, any contributions made on behalf of the employee and increasing the balance maintained in the benefits manager computer;

storing a deductible clause in the benefits manager computer, wherein the deductible clause is for a health insurance policy for the employee from the health insurance company and the terms of the deductible clause specifies financial responsibility for health expenses incurred by the employee, and any amount not responsible for by the health insurance policy would be charged to the employee;

one of the one or more health service providers computers sending a first request to the benefits manager computer over the network for reimbursement for first health services provided to the employee;

comparing, by the benefits manager computer, the first request for reimbursement with the deductible clause to determine financial responsibility for the first health services provided to the employee;

determining, by the benefits manager computer, that the employee is solely responsible for the first health services provided to the employee;

the benefits manager computer deducting the requested reimbursement from the employee's health savings account balance, wherein the resulting balance is negative;

the benefits manager computer transferring the deducted reimbursement to the health service provider computer making the first request to effect an electronic funds transfer therefor;

one of the one or more health service providers computer sending a second request to the benefits manager computer over the network for reimbursement for second health services provided to the employee;

comparing, by the benefits manager computer, the second request for reimbursement with the deductible clause to determine financial responsibility for the second health services provided to the employee;

determining, by the benefits manager computer, that the health insurance policy is responsible for covering at least a portion of the second health services provided to the employee;

the benefits manager computer receiving an electronic funds transfer from the insurance company computer to provide reimbursement for the covered portion;

the benefits manager computer deducting at least some of the outstanding negative balance from the amount for reimbursement to compensate for the employee's negative balance; and the benefits manager computer forwarding any remaining funds received from the insurance company computer to the health service provider computer making the second request to pay for the second health services rendered to the employee.

9. The computer program product of claim 8, wherein a payment host computer is provided between the benefits manager computer and the one or more health service provider computers for processing payment transactions therebetween.

10. The computer program product of claim 9, wherein the payment host computer comprises a Pharmacy Benefits Manager processor.

11. The computer program product of claim 8, wherein the employee's negative balance is restored by a subsequent infusion into the health savings account.

12. The computer program product of claim 8, wherein the health savings account integrates more than one benefit program.

13. The computer program product of claim 8, wherein the health savings account is a tax favored account or not a tax favored account.

14. The computer program product of claim 8, wherein the health savings account is not a tax favored account.

15. A computer implemented system for administering a health saving account, the system comprising:
   respective computers interconnected over a network for providing electronic communications between a benefits manager, a health insurance company, and one or more health service providers;
   the benefits manager computer maintains a balance for a health savings account of the employee;
   the benefits manager computer maintains an increased balance to reflect the benefits manager accepting any contributions made on behalf of the employee;
   the benefits manager computer stores a deductible clause, wherein the deductible clause is for a health insurance policy for the employee from the health insurance company and the terms of the deductible clause specifies financial responsibility for health expenses incurred by the employee, and any amount not responsible for by the health insurance policy would be charged to the employee;
   one of the one or more health service providers computers sends a first request to the benefits manager computer over the network for reimbursement for first health services provided to the employee;
   the benefits manager computer compares the first request for reimbursement with the deductible clause to determine financial responsibility for the first health services provided to the employee;
   the benefits manager computer determines that the employee is solely responsible for the first health services provided to the employee;
   the benefits manager computer deducting the requested reimbursement from the employee's health savings account balance, wherein the resulting balance is negative;
   the benefits manager computer transfers the deducted reimbursement to the health service provider computer making the first request to effect an electronic funds transfer therefor;
   one of the one or more health service providers computer sends a second request to the benefits manager computer over the network for reimbursement for second health services provided to the employee;
   the benefits manager computer compares the second request for reimbursement with the deductible clause to determine financial responsibility for the second health services provided to the employee;
   the benefits manager computer determines that the health insurance policy is responsible for covering at least a portion of the second health services provided to the employee;
   the benefits manager computer receives an electronic funds transfer from the insurance company computer to provide reimbursement for the covered portion;
   the benefits manager computer deducts at least some of the outstanding negative balance from the amount for reimbursement to compensate for the employee's negative balance; and
   the benefits manager computer forwards any remaining funds received from the insurance company computer to the health service provider computer making the second request to pay for the second health services rendered to the employee.

16. The system of claim 15, further comprising a payment host computer provided between the benefits manager computer and the one or more health service provider computers for processing payment transactions therebetween.

17. The system of claim 16, wherein the payment host computer comprises a Pharmacy Benefits Manager processor.

18. The system of claim 16, wherein the employee's negative balance is restored by a subsequent infusion into the health savings account.

19. The system of claim 16, wherein the health savings account integrates more than one benefit program.

20. The system of claim 16, wherein the health savings account is a tax favored account or not a tax favored account.

21. The system of claim 16, wherein the health savings account is not a tax favored account.

* * * * *